United States Patent
Gu et al.

(10) Patent No.: US 8,513,245 B2
(45) Date of Patent: Aug. 20, 2013

(54) PHARMACEUTICAL COMPOSITION FOR REDUCING THE AREA OF MYOCARDIAL INFARCTION AND ITS USE

(75) Inventors: Shuhua Gu, Changzhou (CN); Changlin Mei, Changzhou (CN); Dingfeng Su, Changzhou (CN); Juan Du, Changzhou (CN); Rong Fan, Changzhou (CN)

(73) Assignee: Changzhou Hi-Tech District Multiple Dimension Industry Technology Institute Co., Ltd., Changzhou, Jiangsu (CN)

( * ) Notice: Subject to any disclaimer, the term of this patent is extended or adjusted under 35 U.S.C. 154(b) by 803 days.

(21) Appl. No.: 12/128,568

(22) Filed: May 28, 2008

(65) Prior Publication Data

US 2009/0012096 A1 Jan. 8, 2009

(30) Foreign Application Priority Data

Jul. 3, 2007 (CN) .......................... 2007 1 0025055

(51) Int. Cl.
*A01N 43/58* (2006.01)
*A61K 31/50* (2006.01)
*A61K 31/497* (2006.01)

(52) U.S. Cl.
USPC ........................................ 514/247; 514/252.1

(58) Field of Classification Search
USPC .................... 514/221, 252.13, 331, 634, 369, 514/370, 247, 252.1
See application file for complete search history.

(56) References Cited

U.S. PATENT DOCUMENTS 4,743,621 A * 5/1988 Cavazza ........................ 514/547
6,423,705 B1 * 7/2002 Tracey et al. ................. 514/221

* cited by examiner

*Primary Examiner* — Yong Chong
(74) *Attorney, Agent, or Firm* — Squire Sanders (US) LLP

(57) ABSTRACT

This invention relates to a pharmaceutical composition for preventing and curing myocardium ischemia and reducing area of myocardial infarction, its pharmaceutical preparation and applications. The composition includes (a) levocarnitine or its derivatives, and (b) trimetazidine or its medicative salts. The quantity of levocarnitine or its derivatives, and trimetazidine or its medicative salts in the composition is effective amount for treating myocardial ischemia and reducing the area of myocardial infarction.

20 Claims, No Drawings

PHARMACEUTICAL COMPOSITION FOR REDUCING THE AREA OF MYOCARDIAL INFARCTION AND ITS USE

CROSS REFERENCE TO RELATED APPLICATION

The present application claims priority to Chinese application No. 200710025055.8, which was filed on Jul. 3, 2007. The teachings of the aforementioned Chinese patent application are incorporated herein by reference in its entirety.

FIELD OF THE INVENTION

This invention relates to a medicine field, a medicine for reducing the area of myocardial infarction and its use and pharmaceutical preparation.

DESCRIPTION OF THE BACKGROUND

Myocardial infarction is myocardial necrosis due to persistently ischemia of partial myocardium, which results from atheromatous plaque bleeding and intravascular thrombogenesis caused from coronary atherosclerosis, which can result in rapidly, permanently and completely blocking of lumen of the blood vessel, and discontinuing of the bloodstream. It can be divided into 3 phases according to clinical process and ECG manifestation, which are acute, subacute and chronic phases. The clinical symptoms mainly occur in the acute phase, and the highest mortality is in the first week of the acute phase. Acute myocardial infarction (AMI) is common severe case that threatens human life, and it is also currently one of the most harmful heart diseases.

Both experimental and clinical studies domestically and worldwide have found, that some of the myocardial cell will be irreversible infarcted due to AMI, but the surrounding area of the infarcted myocardium remains partially stunning and hibernating, the myocardium were very fragile, which was named as articulo mortis myocardium. Because of presences of different level dysfunction after AMI, the myocardium will be progressed to further necrosis due to calcium overloading, oxygen free radicals damaging or other metabolic factors influences, and will cause further area enlargement of the infarction. (Journal of Jilin University (Medical Edition). 2002, 23 (6): 659-660). The area of myocardial infarction is the major determinant factor of the short and long-term prognosis for AMI patients.

DETAILED DESCRIPTION OF THE INVENTION

An objective of this invention is to provide a pharmaceutical composition for reducing the area of myocardial infarction and treating myocardial ischemia.

Another objective of this invention is to provide a clinical applicable pharmaceutical preparation for reducing the area of myocardial infarction and treating myocardial ischemia.

A further objective of this invention is to provide therapeutic method for reducing the area of myocardial infarction and treating myocardial ischemia.

Researchers of the invention have found that combining trimetazidine hydrochloride and levocarnitine or its derivative, will increase the therapeutic effect of reducing the area of myocardial infarction than using one of the single recipe alone. The pharmaceutical composition has significant synergism, compared with using single recipe alone. This finding has been confirmed by the experiment in example 1, which the weight of rat acute infracted myocardium declined much more than the therapeutic effect of using single recipe of either levocarnitine or trimetazidine alone. The attention should be paid on that the dose of trimetazidine hydrochloride in the composition is inconsistent with the group of using trimetazidine hydrochloride alone, which has dose-effective relationship. The optimal dose ratio is from about 3 mg/kg of trimetazidine hydrochloride and 600 mg/kg of levocarnitine (1:200), and the doses of levocarnitine and trimetazidine hydrochloride in the composition are significantly reduced than the dosage used in the single recipe group, and equivalent therapeutic effect was observed.

The researcher in this invention has also found that the pharmaceutical composition of levocarnitine and trimetazidine is also effective in preventing the enlargement of the area of myocardial infarction, and protecting ischemic myocardium injury. Reducing the dose of single recipe in the composition and obtained equivalent therapeutic effect, which is useful in reducing side effect of the drug. So the invention here has provided an efficient and safe pharmaceutical composition for treating human ischemic heart disease.

Based on the finding above, the invention has provided a pharmaceutical composition for preventing and curing ischemic cardiac disease in reducing the area of AMI. The composition comprises 1) levocarnitine or its derivatives, and 2) trimetazidine or its medicative salts. The doses of the levocarnitine and trimetazidine in the composition are effective therapeutic doses in reducing the area of AMI.

Anti-myocardial ischemia action stands for "reducing the area of myocardial infarction" in this invention, which denoted as declined weight of infarcted myocardium. "Quantity of effectively reducing the area of myocardial infarction" stands for reducing the area of AMI at greater than or equal to 1% that the composition acts, subtracting the effect of reducing area of AMI that either trimetazidine or levocarnitine acts alone (the action of reduced area of AMI in single recipe of either levocarnitine or trimetazidine alone is calculated as baseline). In some cases, it also means that the reduced area of AMI at greater than or equal to 5%, 10%, 15%, 20%, 30%, 35%, 40% and 50%.

In the pharmaceutical composition of this invention, the levocarnitine or derivatives thereof include but not limit to, levocarnitine, and also acetyl levocarnitine, propionyl levocarnitine and their pharmaceutically acceptable salts. The levocarnitine or derivatives thereof are preferably levocarnitine, acetyl levocarnitine and their pharmaceutically acceptable salts; especially preferably is levocarnitine.

In the compositions of this invention, a preferred trimetazidine or its pharmaceutically acceptable salt is trimetazidine hydrochloride, which is to compose with levocarnitine or its derivatives and pharmaceutically acceptable salts to form a pharmaceutical composition described herein.

The pharmaceutically acceptable salts in this invention include salt forming reaction that levocarnitine or its derivatives and trimetazidine with inorganic and organic acid. Those inorganic and organic acids are included as following: hydrochloride acid, hydrobromide acid, hydriodic acid, sulphuric acid, nitric acid, phosphoric acid, acetic acid, maleic acid, maleic acid, maleic acid, oxalic acid, oxalic acid, tartaric acid, malic acid, mandelic acid, trifluoroacetic acid, pantothenic acid, methane sulfonic acid, or para-toluenesulfonic acid.

In the compositions of this invention, the levocarnitine or its derivatives have synergies with trimetazidine or its pharmaceutically acceptable salts. Therefore, in this invention the weight ratio of levocarnitine or its derivatives with trimetazidine or its pharmaceutically acceptable salts are one of the important technical features. Generally, in the compositions of the invention, the weight ratio of levocarnitine and trimetazidine or its pharmaceutically acceptable salts is about 1:0.000016 to 1:0.4, for example about 1:0.001-0.1, about 1:0.001-0.01, about 1:0.005-0.01, or about 1:0.005. In some examples, the compositions may exclude any of the weight ratios of levocarnitine or its derivatives with trimetazidine or its pharmaceutically acceptable salts mentioned above. For example, in some cases the composition may especially exclude weight ratios of levocarnitine or its derivatives and trimetazidine or its pharmaceutically acceptable salts as in 1:0.01, 1:0.02 or 1:0.03.

This invention also provides a pharmaceutical preparation, which includes trimetazidine and its pharmaceutically acceptable salts, especially preferably trimetazidine hydrochloride form, one of the forms and levocarnitine or its derivatives and pharmaceutical acceptable salts, either combining or mixing with pharmaceutical acceptable carries, excipient or thinner, to form two pharmaceutical acceptable separately packed formulation. The method of compositional administration is according to pharmaceutical regulation of the solo administration based drug combination mode. Or it can be a mixture of the combination in one package as in this invention, either combining or mixing with pharmaceutical acceptable carries, excipient or thinner, to form pharmaceutical acceptable formulation; administration mode is according to pharmaceutical regulation.

The pharmaceutical formulation of this invention preferably contains active ingredients containing levocarnitine or its derivatives and trimetazidine or its salts with one or several pharmaceutical acceptable carries, wherein the weight ratio of levocarnitine or its derivatives with trimetazidine or its salts is about 1:0.000016 to 1:0.4, such as about 1:0.01-0.1, about 1:0.001-0.01, about 1:0.005-0.01, or about 1:0.005.

In the pharmaceutical preparations in the invention, an especially preferred case is pharmaceutical preparation formed by levocarnitine and trimetazidine or its pharmaceutically acceptable salt.

The pharmaceutical preparation in the invention can be administered orally or parenterally. Parenteral administrations include intravenous, intramuscular, intraperitoneal, hypodermical, rectal, and regional administration.

The pharmaceutical preparations in this invention can be oral administration, such as tablet, sustained-release tablet, pastille, oil or aqueous suspension, granules, emulsion, hard or soft capsules, or syrup form.

Oral administration in this invention can be obtained by any known method for preparing oral administration of pharmaceutical composition, and such pharmaceutical composition contains one or more substances selected from following: sweetening agent, correctant, colorant and preservative, in order to reach better pharmacy appearance and palatable purposes.

Troche contains active ingredients and its mixture of pharmaceutical acceptable excipients that suitable for troche preparation. These excipients can be as: inertia thinner such as calcium carbonate, sodium carbonate, lactose, calcium phosphate or sodium phosphate; granules and disintegrants include microcrystalline cellulose, sodium carboxymethyl cellulose, cornstarch or alginic acid; binders includes starch, gelatin, polyvidone or acacia gum; lubricator includes magnesium stearate, stearic acid or talcum powder.

Troche can be in a non-coating form, or coating form that can be obtained by any known method in the field for concealing the unpleasant taste and delaying the time of its disintegration and absorption in gastrointestinal tract, which can extend the effective time period of the drug. For example, water-soluble material for concealing the unpleasant taste, such as hydroxy-propyl methyl cellulose of hydroxypropyl cellulose or the material for delay releasing time such as ethyl cellulose, cellulose acetate butyrate.

The oral delivery drug form in this invention also can be provided as glutoid capsule, wherein the active ingredients can be mixed with the inertia solid thinner such as calcium carbonate, calcium phosphate and kaolin; or can be provided as soft gels, wherein the active ingredients mixed with the water-soluble carrier such as polyethylene glycol; or oil medium such as peanut oil, liquid paraffin or olive oil.

The water suspension of this invention contains active ingredients and the mixture of excipients or dispersants which is suitable for preparing aqueous suspension. Such excipients include suspension such as sodium carboxymethyl cellulose, methyl cellulose, hydroxypropoxyl methyl cellulose, sodium alginate, polyvidone, tragacanth gum and acacia gum. The dispersant includes natural phospholipids such as lecithin, or condensation product of alkylene oxide and fatty acid, such as polyoxyethylene stearates, or condensation product of alkylene oxide and long chain adipic alcohol such as heptadeca-polyoxyethylene cetyl alcohol, or condensation product of alkylene oxide and the partial ester which derived from the fat and hexitol, such as poly-oxethane sorbitan monooleate.

The injection preparation in this invention can be aseptic injection powder that contains active ingredients, which can be dissolved in water or organic solvents such as ethanol, methanol, acetone, chloroform etc., it can be exsiccated at room temperature or lyophilizated to obtained aseptic injection powder or crystal.

The solvent of the injection preparation in this invention is aseptic injection solution that contains active ingredients. Such aseptic injection solution can be made from water, Ringer's solution, sodium chloride solution and/or glucose solution as carrier.

The injection preparation in this invention can be introduced to bloodstream or other part of the body of the patient through bolus injection; or can be introduced to bloodstream of patient by intravenous drop infusion Alternatively, this invention also provides a method for preparing pharmaceutical preparation, which comprises mixing the pharmaceutical composition mentioned above with one or several pharmaceutical acceptable carries or excipients.

This invention further provides a method for reducing the area of myocardial infarction, which comprises introducing trimetazidine or its pharmaceutical acceptable salts with Levocarnitine or its derivatives and pharmaceutical acceptable salts to AMI patient, either respectively or simultaneously, or introducing the pharmaceutical composition or its preparation to AMI patient, in order to reach the aim of reducing the area of AMI, and preventing episode attack. The preferred active ingredients in the invention are levocarnitine or its derivatives and trimetazidine or its pharmaceutical acceptable salts with one or several pharmaceutical carries. The weight ratio of levocarnitine or its derivatives and trimetazidine or its pharmaceutical acceptable salts is about 1:0.000016 to 1:0.4, e.g. about 1:0.001-0.1, or about 1:0.001-0.01, or about 1:0.005-0.01, or about 1:0.005.

An especially preferred pharmaceutical preparation in the invention is composition of levocarnitine and trimetazidine or with its pharmaceutically acceptable salts. Daily dose for adult is that 5-300 mg/kg of levocarnitine or its derivatives; 0.005-1 mg/kg of trimetazidine or its pharmaceutically acceptable salts This invention also provides a method for treating and preventing other myocardial ischemia and various of illness or symptoms that caused by myocardial ischemia, such as cardiogenic shock, hemorrhagic shock, chronic myocardial infarction, angina, heart pump failure, acute coronary syndrome, acute or chronic heart failure etc histocyte energy metabolic abnormality caused by myocardial ischemia. Preferred active ingredients are levocarnitine or its derivatives and trimetazidine or its pharmaceutically acceptable salts with one or more kinds of pharmaceutical carries, wherein the weight ratio of levocarnitine or its derivatives and trimetazidine or its pharmaceutically acceptable salts is about 1:0.000016 to 1:0.4, e.g. about 1:0.001-0.1, about 1:0.001-0.01, about 1:0.005-0.01, or about 1:0.005.

In the pharmaceutical preparation in the invention, an especially preferred pharmaceutical preparation comprises levocarnitine and trimetazidine with their pharmaceutically acceptable salts. Adult Daily dose for adult is that 5-600 mg/kg of levocarnitine or its derivatives; 0.005-3 mg/kg of trimetazidine or its pharmaceutical acceptable salts.

In some cases, this invention should exclude the following contents: therapeutic alliance for treating post myocardial infarction pump failure, which separately introduces 2000 mg of levocarnitine via intravenous injection, one time a day; and 20 mg/per time of trimetazidine by oral administration, three times a day. The weight ratios of levocarnitine and trimetazidine in the therapeutic alliance are 1:0.01, 1:0.02 or 1:0.03.

EXAMPLES

The following examples are only for illustration of the invention and shall not be construed to limit the scope of the present invention.

Example 1

The protections effect of trimetazidine hydrochloride, Levocarnitine; and different ratios of composition of trimetazidine hydrochloride and Levocarnitine in rat model of AMI.
Experimental Grouping:

Trimetazidine hydrochloride and Levocarnitine, each drug group was divided into four subgroups, and a solvent control group, five groups in total, as following:

trimetazidine hydrochloride (TMZ): 1 mg/kg, 3 mg/kg, 6 mg/kg, 9 mg/kg and solvent control group
Levocarnitine (LC): 100 mg/kg, 300 mg/kg, 600 mg/kg, 900 mg/kg and solvent control group The selection of combination doses of trimetazidine hydrochloride and levocarnitine were based on the two drugs' efficacy when they are acting alone, exclude the two large doses, the trimetazidine hydrochloride and levocarnitine compound dosage (mg/kg) are as following: 3+100 group, 3+300 group, 3+600 group, 1+300 group, 6+300 group and solution control group.

Method and Experimental Conditions

SD male rats, average weight at 200±20 g were used as model animals for the experiment. Rats were weighed firstly, drugs as planned in each dosage group above were delivered via intraperitoneal injection, with injection dose of 5 ml/kg. Immediately use ether for anesthesia, fixed rat on the experimental table, sterilizing the left side of breast skin with 75% alcohol, open the chest between the $3^{rd}$ to $4^{th}$ ribs followed left limit of sternal border. Cutting open the pericardium, the heart was revealed, find anterior descending coronary in between pulmonary conus and left auricle, using undamaging round sewing needle of no. 6/0 and silk suture to thread through the place at 2 mm from the beginning of anterior descending coronary and ligat the vessel. AMI model was completed. Execute the rat by head-breaking method four hours after the AMI model was made. Removed the heart out, washed with saline and dehematized, blotted with filter paper, weighed entire heart and left ventricle after cutting out of auricle of heart and right ventricle. Cut left ventricle into myocardium pieces in thickness of 2 mm each, incubating in 0.1% NBT solution for 15-20 mins at 37° C. Make sure that each myocardium pieces were in contact completely with staining solution during the incubation. Wash off the redundant of dye after 20 mins. The infarcted myocardium were not stained, while none infracted myocardium were stained in dark blue. Cut off stained myocardium, and weighed none stained infarcted myocardium. The result was analyzed by calculating the weight ratio of infracted myocardium weight (IMW) to heart weight (HW), which were shown as below.

1. Trimetazidine hydrochloride only group: in comparison with solvent control group, follow the dose of trimetazidine hydrochloride increasing, the infracted myocardium weight were reduced, a good dose-effective relationship has been observed. The IMW/HW (%) of 9 mg/kg of trimetazidine group was 16.0, which has reduced 34.7% in comparison with solvent control group of 24.5%, which has shown in table 1.

TABLE 1

Protective effect of trimetazidine hydrochloride in rat model of AMI

| Groups/dose (mg/kg) | n | weight (g) | HW (mg) | IMW (mg) | IMW/HW (%) |
|---|---|---|---|---|---|
| Cont group | 13 | 200 ± 8.05 | 792 ± 80.4 | 193 ± 46.3 | 24.5 ± 5.24 |
| TMZ 1 mg/kg | 13 | 195 ± 11.4 | 783 ± 70.9 | 177 ± 20.2 | 22.8 ± 3.40 |
| TMZ 3 mg/kg | 13 | 195 ± 7.23 | 794 ± 48.2 | 163 ± 20.2* | 21.0 ± 2.60* |
| TMZ 6 mg/kg | 14 | 200 ± 11.6 | 778 ± 55.0 | 132 ± 19.1*** | 17.0 ± 3.20*** |
| TMZ 9 mg/kg | 12 | 199 ± 10.4 | 798 ± 38.1 | 125 ± 15.2* | 16.0 ± 2.50* | vs control group
*P < 0.05
***P < 0.001

2. Levocarnitine only group: the results were similar as the single use of trimetazidine hydrochloride, follow the dose of levocarnitine increasing, the infracted myocardium weight reduced, it also has a good dose-effective relationship. The IMW/HW (%) of 900 mg/kg of levocarnitine group has reduced 22.9% in comparison with solvent control group, which has shown in table 2.

TABLE 2

The protective effect of levocarnitine in rat model of AMI

| groups/dose (mg/kg) | n | Weight (g) | HW (mg) | IMW (mg) | IMW/HW (%) |
|---|---|---|---|---|---|
| Cont group | 10 | 203 ± 10.8 | 835 ± 38.4 | 171 ± 38.4 | 20.5 ± 4.68 |
| LC 100 mg/kg | 10 | 202 ± 8.50 | 830 ± 49.0 | 139 ± 25.9* | 16.8 ± 3.33 |
| LC 300 mg/kg | 11 | 202 ± 5.24 | 822 ± 51.4 | 141 ± 23.0 | 17.2 ± 3.04 |
| LC 600 mg/kg | 12 | 202 ± 9.38 | 836 ± 58.5 | 139 ± 24.0* | 16.8 ± 3.10* |
| LC 900 mg/kg | 11 | 205 ± 8.72 | 821 ± 54.7 | 129 ± 23.8** | 15.8 ± 3.10* | vs control group
*$P < 0.05$
**$P < 0.01$

3. Combination group of trimetazidine hydrochloride and levocarnitine in different ratios: the results were shown that both groups of 3 mg/kg of trimetazidine hydrochloride combined with 300 mg/kg of levocarnitine, and of 3 mg/kg of trimetazidine hydrochloride combined with 600 mg/kg of levocarnitine had effective results. In comparison with control group, the percentage of infarcted myocardium weight to heart weight has reduced at 21.2% and 36.9% respectively. Attention should be paid to the group using trimetazidine hydrochloride alone, where trimetazidine hydrochloride has shown dose effective relationship in reducing the area of AMI, while the highest dose of trimetazidine in the combination group did not give the best result of reducing effect of AMI, which has shown in table 3.

TABLE 3

Protective effect of levocarnitine and trimetazidine hydrochloride at different ratio in rat model of AMI

| Groups/dose (mg/kg) | n | Weight (g) | HW (mg) | IMW (mg) | IMW/HW (%) |
|---|---|---|---|---|---|
| Cont group | 14 | 172 ± 9.80 | 778 ± 79.5 | 189 ± 20.9 | 24.1 ± 2.86 |
| TMZ 3 + LC100 | 14 | 173 ± 5.95 | 751 ± 36.6 | 167 ± 17.6** | 22.2 ± 1.97* |
| TMZ3 + LC300 | 18 | 176 ± 5.80 | 779 ± 76.3 | 148 ± 23.1*** | 19.0 ± 2.24*** |
| TMZ 3 + LC600 | 14 | 190 ± 8.50 | 787 ± 66.8 | 119 ± 14.6*** | 15.2 ± 1.52*** |
| TMZ1 + LC300 | 12 | 168 ± 13.2 | 760 ± 81.6 | 177 ± 12.3 | 23.4 ± 2.05 |
| TMZ 6 + LC300 | 14 | 177 ± 12.0 | 775 ± 46.5 | 157 ± 21.8* | 20.3 ± 3.02 | vs control group
*$P < 0.05$
**$P < 0.01$

Example 2

The Protective Effect of Combination Group of Different Doses in Rat Model of AMI The dosage of trimetazidine hydrochloride and levocarnitine was designed according to the pharmacodynamics of the two drugs, taking off two largest dose groups, the dose (mg/kg) setting of trimetazidine hydrochloride and levocarnitine and results are shown in table 4.

TABLE 4

The protective effect of different doses of combinations in rat model of AMI

| groups/dose (mg/kg) | n | Weight (g) | HW (mg) | IMW (mg) | IMW/HW (%) |
|---|---|---|---|---|---|
| Control group | 14 | 172 ± 9.80 | 778 ± 79.5 | 189 ± 20.9 | 24.1 ± 2.86 |
| LC600 + TMZ 2.4 | 14 | 185 ± 8.10 | 777 ± 77.9 | 124 ± 12.3 | 16.0 ± 1.12*** |
| LC600 + TMZ 1.2 | 14 | 179 ± 6.50 | 769 ± 68.5 | 131 ± 18.4 | 17.1 ± 2.35*** |
| LC600 + TMZ1 | 14 | 169 ± 8.10 | 779 ± 52.3 | 142 ± 21.5 | 18.2 ± 2.10*** |
| LC600 + TMZ0.3 | 14 | 180 ± 8.90 | 787 ± 74.5 | 179 ± 17.2 | 22.8 ± 1.22*** |
| LC600 + TMZ3.6 | 14 | 187 ± 7.20 | 759 ± 49.2 | 116 ± 16.9 | 15.3 ± 1.92*** |
| LC600 + TMZ4.2 | 14 | 166 ± 6.50 | 775 ± 52.9 | 122 ± 20.5 | 15.8 ± 2.42*** |
| LC600 + TMZ4.8 | 14 | 181 ± 8.50 | 753 ± 57.1 | 127 ± 12.7 | 16.9 ± 2.15*** |
| LC600 + TMZ5.4 | 14 | 181 ± 10.80 | 798 ± 42.1 | 150 ± 19.4 | 18.8 ± 2.11*** |
| LC300 + TMZ9 | 14 | 169 ± 8.40 | 768 ± 44.7 | 163 ± 17.7 | 21.2 ± 2.45*** |

TABLE 4-continued

The protective effect of different doses of combinations in rat model of AMI

| groups/dose (mg/kg) | n | Weight (g) | HW (mg) | IMW (mg) | IMW/HW (%) |
|---|---|---|---|---|---|
| LC300 + TMZ15 | 14 | 172 ± 9.50 | 778 ± 84.2 | 163 ± 15.4 | 20.9 ± 1.41*** |
| LC300 + TMZ24 | 14 | 174 ± 8.30 | 765 ± 62.2 | 149 ± 11.9 | 19.5 ± 1.82*** |
| LC300 + TMZ30 | 14 | 1850 ± 6.50 | 776 ± 71.1 | 149 ± 22.4 | 19.2 ± 1.42*** | vs control group
*P < 0.05
**P < 0.01

Example 3

Different Doses of Pharmaceutical Preparation in the Compositions of Trimetazidine Hydrochloride and Levocarnitine The composition of levocarnitine and trimetazidine hydrochloride in this invention can be prepared as following different dosage composition:

Levocarnitine 10 mg-600 mg/kg per day; trimetazidine hydrochloride 0.01 mg-3 mg/kg per day The ratio range from 30 g:1 mg to 0.5 g: 200 mg

| Levocarnitine:trimetazidine hydrochloride | Levocarnitine (w):trimetazidine hydrochloride (w) |
|---|---|
| 1:0.000016 | 1000 g:16 mg |
| 1:0.00004 | 1000 g:40 mg |
| 1:0.00005 | 1000 g:50 mg |
| 1:0.0001 | 1000 g:100 mg |
| 1:0.0005 | 1000 g:500 mg |
| 1:0.001 | 1000 g:1 g |
| 1:0.002 | 1000 g:2 g |
| 1:0.003 | 1000 g:3 g |
| 1:0.004 | 1000 g:4 g |
| 1:0.005 | 1000 g:5 g |
| 1:0.006 | 1000 g:6 g |
| 1:0.007 | 1000 g:7 g |
| 1:0.008 | 1000 g:8 g |
| 1:0.009 | 1000 g:9 g |
| 1:0.02 | 1000 g:20 g |
| 1:0.05 | 1000 g:50 g |
| 1:0.1 | 1000 g:100 g |
| 1:0.2 | 1000 g:200 g |
| 1:0.4 | 1000 g:400 g |
| 1:0.000016 | 1000 g:16 mg |

Example (1)

Oral Solution of Composition of Levocarnitine and Trimetazidine Hydrochloride

Formulation

| Levocarnitine | 1000 g |
| Trimetazidine hydrochloride | 0.016 g |
| Distilled water | add up to 10000 ml |

Method of Preparation:

Dissolving Levocarnitine and trimetazidine hydrochloride in 3000 ml distilled water, then adding distilled water to 10000 ml.

| 1:0.00004 | 1000 g:40 mg |

Example (2)

Oral Solution of Composition of Levocarnitine and Trimetazidine Hydrochloride Formulation

| Levocarnitine | 1000 g |
| Trimetazidine hydrochloride | 0.04 g |
| Distilled water | add up to 10000 ml |

Method of Preparation:

Dissolving Levocarnitine and trimetazidine hydrochloride in 3000 ml distilled water, then adding distilled water up to 10000 ml.

| 1:0.00005 | 1000 g:50 mg |

Example (3)

Oral Solution of Composition of Levocarnitine and Trimetazidine Hydrochloride

Formulation:

| Levocarnitine | 1000 g |
| Trimetazidine hydrochloride | 0.05 g |
| Distilled water | add up to 10000 ml |

Method of Preparation:

Dissolving Levocarnitine and trimetazidine hydrochloride in 3000 ml distilled water, then adding distilled water up to 10000 ml, i.e.

| 1:0.0001 | 1000 g:100 mg |

Example (4)

Syrup of Composition of Levocarnitine and Trimetazidine Hydrochloride

Formulation:

| | |
|---|---|
| Levocarnitine | 1000 g |
| Trimetazidine hydrochloride | 0.1 g |
| Distilled water | 150 ml |
| Simple syrup | add up to 10000 ml |

Method of Preparation:

Dissolving Levocarnitine and trimetazidine hydrochloride in distilled water, adding simple syrup to 10000 ml.

| | |
|---|---|
| 1:0.0005 | 1000 g:500 mg |

Example (5)

Emulsion of Composition of Levocarnitine and Trimetazidine Hydrochloride

Formulation:

| | |
|---|---|
| Levocarnitine | 1000 g |
| Trimetazidine hydrochloride | 0.5 g |
| Gum Arabic fine powder | 125 g |
| Gum tragacanth fine powder | 7 g |
| Saccharin Sodium | 0.1 g |
| Almond oil | 1 ml |
| Ethylparaben | 0.5 g |
| Distilled water | add up to 1000 ml |

Method of Preparation:

Grind Levocarnitine, trimetazidine dihydrochloride and gum Arabic powder in uniform, add 250 ml distilled water, grind and follow to one direction to form milky, add saccharin sodium solution, almond oil, methylparaben solution, then add gum tragacanth powder slowly, finally add distilled water up to 1000 ml.

| | |
|---|---|
| 1:0.002 | 1000 g:2 g |

Example (6)

Injection of Composition of Levocarnitine and Trimetazidine Hydrochloride

Formulation:

| | |
|---|---|
| Levocarnitine | 500 g |
| Trimetazidine hydrochloride | 1 g |
| Disodium edetate | 0.5 g |
| Hydrochloric acid | 20 g |
| Water for injection | add up to 1000 ml |

Method of Preparation:

Adding 80% of injection water in a container, dissolving Levocarnitine and trimetazidine hydrochloride in it, and add sodium bicarbonate in fractionation gradually, stirring until they were dissolved completely; add disodium edetate prepared in advance and hydrochloric acid, stirring to uniform, adjusting the solution pH to 6.0~6.2, finally adding injection water up to 1000 ml, decolorizing with 0.1% active carbon, filtrating in melting glass filter and membrane filter, and encapsulating under nitrogen stream, and finally sterilizing in 100□ flowing steam for 15 minutes.

| | |
|---|---|
| 1:0.005 | 1000 g:5 g |

Example (7)

Injection of Composition of Levocarnitine and Trimetazidine Hydrochloride

Formulation:

| | |
|---|---|
| Levocarnitine | 600 g |
| Trimetazidine hydrochloride | 3 g |
| Disodium edetate | 0.5 g |
| Hydrochloric acid | 20 g |
| Water for injection | add up to 1000 ml |

Method of Preparation:

Adding 80% of injection water in the container, dissolving Levocarnitine and trimetazidine hydrochloride in it, adding sodium bicarbonate gradually, stirring to dissolving completed, adding disodium edetate and hydrochloric acid, stirring to uniform, adjusting the solution pH to 6.0~6.2, adding injection water up to 1000 ml, decolorizing with active carbon, filtrating, encapsulating, sterilizing.

| | |
|---|---|
| 1:0.005 | 1000 g:5 g |

Example (8)

Injection of Composition of Levocarnitine and Trimetazidine Hydrochloride

Formulation:

| | |
|---|---|
| Levocarnitine | 400 g |
| Trimetazidine hydrochloride | 2 g |
| Disodium edetate | 0.5 g |
| Hydrochloric acid | 20 g |
| Water for injection | add up to 1000 ml |

Method of Preparation:

Adding 80% of injection water in the container, dissolving Levocarnitine and trimetazidine hydrochloride in it, adding sodium bicarbonate gradually, stirring to dissolving completed, adding disodium edetate and hydrochloric acid, stirring to uniform, adjusting the solution pH to 6.0~6.2, adding injection water up to 1000 ml, decolorizing with active carbon, filtrating, encapsulating, sterilizing.

| 1:0.005 | 1000 g:5 g |
|---|---|

Example (9)

Injection of Composition of Levocarnitine and Trimetazidine Hydrochloride

Formulation:

| | |
|---|---|
| Levocarnitine | 200 g |
| Trimetazidine hydrochloride | 1 g |
| Disodium edetate | 0.5 g |
| Hydrochloric acid | 20 g |
| Water for injection | add up to 1000 ml |

Method of Preparation:

Adding 80% of injection water in the container, dissolving Levocarnitine and trimetazidine hydrochloride in it, adding sodium bicarbonate gradually, stirring to dissolving completed, adding disodium edetate and hydrochloric acid, stirring to uniform, adjusting the solution pH to 6.0~6.2, adding injection water up to 1000 ml, decolorizing with active carbon, filtrating, encapsulating, sterilizing.

| 1:0.005 | 1000 g:5 g |
|---|---|

Example (10)

Transfusion of Composition of Levocarnitine and Trimetazidine Dihydrochloride

Formulation

| | |
|---|---|
| Levocarnitine | 600 g |
| Trimetazidine dihydrochloride | 5 g |
| Disodium edetate | 5 g |
| Hydrochloric acid | 200 g |
| Water for injection | add up to 10000 ml |

Method of Preparation:

Dissolving Levocarnitine, trimetazidine dihydrochloride in 8000 ml of water for injection, stirring mixing till they were dissolved completely, adding antioxidant and adjusting the pH to around 6.0 with 10% hydrochloric acid, adding some injection water, and then decolorizing with 0.15% active carbon, filtrating the solution to pellucid, encapsulating and filling into the 10 ml of bottle under nitrogen. The filled bottle is covered with a lid, packaging and sterilizing in 100□ for 30 minutes.

| 1:0.001 | 1000 g:1 g |
|---|---|

Example (11)

Transfusion of Composition of Levocarnitine and Trimetazidine Dihydrochloride

Formulation:

| | |
|---|---|
| Levocarnitine | 1000 g |
| Trimetazidine dihydrochloride | 1 g |
| Disodium edentate | 5 g |
| Hydrochloric acid | 200 g |
| Water for injection | add up to 10000 ml |

Method of Preparation:

Dissolving Levocarnitine, trimetazidine dihydrochloride in 8000 ml of water for injection, stirring mixing till they were dissolved completely, adding antioxidant and adjusting the pH to around 6.0 with 10% hydrochloric acid, adding some injection water, and then decolorizing with 0.15% active carbon, filtrating the solution to pellucid, encapsulating and filling into the 100 ml of bottle under nitrogen. The filled bottle is covered with a lid, packaging and sterilizing in 100□ for 30 minutes.

| 1:0.002 | 1000 g:2 g |
|---|---|

Example (12)

Transfusion of Composition of Levocarnitine and Trimetazidine Dihydrochloride

Formulation:

| | |
|---|---|
| Levocarnitine | 1000 g |
| Trimetazidine dihydrochloride | 2 g |
| Disodium edentate | 5 g |
| Hydrochloric acid | 200 g |
| Water for injection | add up to 10000 ml |

Method of Preparation:

Dissolving Levocarnitine, trimetazidine dihydrochloride in 8000 ml of water for injection, stirring mixing till they were dissolved completely, adding antioxidant and adjusting the pH to around 6.0 with 10% hydrochloric acid, adding some injection water, and then decolorizing with 0.15% active carbon, filtrating the solution to pellucid, encapsulating and filling into the 100 ml of bottle under nitrogen. The filled bottle is covered with a lid, packaging and sterilizing in 100□ for 30 minutes.

| 1:0.003 | 1000 g:3 g |
|---|---|

Example (13)

Transfusion of Composition of Levocarnitine and Trimetazidine Dihydrochloride Formulation:

| | |
|---|---|
| Levocarnitine | 1000 g |
| Trimetazidine dihydrochloride | 3 g |
| Disodium edentate | 5 g |
| Hydrochloric acid | 200 g |
| Water for injection | add up to 10000 ml |

Method of Preparation:

Dissolving Levocarnitine, trimetazidine dihydrochloride in 8000 ml of water for injection, stirring mixing till they were dissolved completely, adding antioxidant and adjusting the pH to around 6.0 with 10% hydrochloric acid, adding some injection water, and then decolorizing with 0.15% active carbon, filtrating the solution to pellucid, encapsulating and filling into the 100 ml of bottle under nitrogen. The filled bottle is covered with a lid, packaging and sterilizing in 100□ for 30 minutes.

| | |
|---|---|
| 1:0.004 | 1000 g:4 g |

Example (14)

Transfusion of Composition of Levocarnitine and Trimetazidine Dihydrochloride Formulation:

| | |
|---|---|
| Levocarnitine | 1000 g |
| Trimetazidine dihydrochloride | 4 g |
| Disodium edentate | 5 g |
| Hydrochloric acid | 200 g |
| Water for injection | add up to 10000 ml |

Method of Preparation:

Dissolving Levocarnitine, trimetazidine dihydrochloride in 8000 ml of water for injection, stirring mixing till they were dissolved completely, adding antioxidant and adjusting the pH to around 6.0 with 10% hydrochloric acid, adding some injection water, and then decolorizing with 0.15% active carbon, filtrating the solution to pellucid, encapsulating and filling into the 100□ ml of bottle under nitrogen. The filled bottle is covered with a lid, packaging and sterilizing in 100 for 30 minutes.

| | |
|---|---|
| 1:0.01 | 1000 g:10 g |

Example (15)

Injection of Composition of Levocarnitine and Trimetaxidine Dihydrochloride in Sterilized Gelsiccation Form Formulation:

| | |
|---|---|
| Levocarnitine | 1000 g |
| Trimetazidine dihydrochloride | 10 mg |
| Hydrolyzed Gelatin | 5 ml |
| Mannitol | 10 mg |
| Calcium gluconate | 1 mg |
| Cysteine | 0.5 mg |

Method of Preparation:

Dissolving the ingredients above with injection water, and filtering the solution at aseptic condition; filling into ampoules, obturating after freeze-drying, and checking if there is gas leaking.

| | |
|---|---|
| 1:0.005 | 1000 g:5 g |

Example (16)

Granules of Composition of Levocarnitine and Trimetazidine Dihydrochloride

Formulation:

| | |
|---|---|
| Levocarnitine | 2000 g |
| Trimetazidine dihydrochloride | 10 g |
| PVP K30 | 10 g |
| Cross linking PVP | 15 g |
| Lactose | 1000 g |
| Sucrose | 1000 g |
| Tartrazine | 1 g |
| Stearic acid | 20 g |

Method of Preparation:

Filtrating Levocarnitine and trimetaxidine dihydrochloride with 80# mesh screen, mixing the filtrated solution with lactose and sucrose to uniform, adding PVP K30 solution contains Tartrazine, forming grains with 14# mesh screen, and drying at 70□ to 80□, then forming granules with 12# mesh screen, adding crosslinking PVP and stearic acid and mixing the ingredients to uniform, and packing in 1000 packs.

| | |
|---|---|
| 1:0.006 | 1000 g:6 g |

Example (17)

Granules of Composition of Levocamitine and Trimetazidine Dihydrochloride

Formulation for Making 100 Tablets:

| | |
|---|---|
| Levocarnitine | 2000 g |
| Trimetazidine dihydrochloride | 12 g |
| PVP K30 | 10 g |
| Crosslinking PVP | 15 g |
| Lactose | 1000 g |
| Sucrose | 1000 g |
| Tartrazine | 1 g |
| Stearic acid | 20 g |

Method of Preparation:

Filtrating Levocamitine and trimetaxidine dihydrochloride with 80# mesh screen, mixing the filtrated solution with lactose and sucrose to uniform, adding PVP K30 solution contains Tartrazine, forming grains with 14# mesh screen, and drying at 70□ to 80□, then forming granules with 12# mesh screen, adding crosslinking PVP and stearic acid and mixing the ingredients to uniform, and packing in 1000 packs.

| | |
|---|---|
| 1:0.007 | 1000 g:7 g |

Example (18)

Granules of Composition of Levocarnitine and Trimetazidine Dihydrochloride

Formulation:

| | |
|---|---|
| Levocarnitine | 2000 g |
| Trimetazidine dihydrochloride | 14 g |
| PVP K30 | 10 g |
| Crosslinking PVP | 15 g |
| Lactose | 1000 g |
| Sucrose | 1000 g |
| Tartrazine | 1 g |
| Stearic acid | 20 g |

Method of Preparation:

Filtrating Levocamitine and trimetaxidine dihydrochloride with 80# mesh screen, mixing the filtrated solution with lactose and sucrose to uniform, adding PVP K30 solution contains Tartrazine, forming grains with 14# mesh screen, and drying at 70□ to 800□, then forming granules with 12# mesh screen, adding crosslinking PVP and stearic acid and mixing the ingredients to uniform, and packing in 1000 packs.

| | |
|---|---|
| 1:0.008 | 1000 g:8 g |

Example (19)

Granules Compound of Levocamitine and Trimetazidine Dihydrochloride

Ingredients:

| | |
|---|---|
| Levocarnitine | 2000 g |
| Trimetazidine dihydrochloride | 16 g |
| PVP K30 | 10 g |
| Crosslinking PVP | 15 g |
| Lactose | 1000 g |
| Sucrose | 1000 g |
| Tartrazine | 1 g |
| Stearic acid | 20 g |

Method of Preparation:

Filtrating Levocamitine and trimetaxidine dihydrochloride with 80# mesh screen, mixing the filtrated solution with lactose and sucrose to uniform, adding PVP K30 solution contains Tartrazine, forming grains with 14# mesh screen, and drying at 70□ to 80□, then forming granules with 12# mesh screen, adding crosslinking PVP and stearic acid and mixing the ingredients to uniform, and packing in 1000 packs.

| | |
|---|---|
| 1:0.009 | 1000 g:9 g |

Example (20)

Granules of Composition of Levocamitine and Trimetazidine Dihydrochloride

Formulation:

| | |
|---|---|
| Levocarnitine | 2000 g |
| Trimetazidine dihydrochloride | 18 g |
| PVP K30 | 10 g |
| Crosslinking PVP | 15 g |
| Lactose | 1000 g |
| Sucrose | 1000 g |
| Tartrazine | 1 g |
| Stearic acid | 20 g |

Method of Preparation:

Filtrating Levocamitine and trimetaxidine dihydrochloride with 80# mesh screen, mixing the filtrated solution with lactose and sucrose to uniform, adding PVP K30 solution contains Tartrazine, forming grains with 14# mesh screen, and drying at 70□ to 80□, then forming granules with 12# mesh screen, adding crosslinking PVP and stearic acid and mixing the ingredients to uniform, and packing in 1000 packs.

| | |
|---|---|
| 1:0.001 | 1000 g:1 g |

Example (21)

Troche of Composition of Levocarnitine and Trimetazidine Dihydrochloride

Formulation (for 1000 Tablets):

| | |
|---|---|
| Levocarnitine | 1000 g |
| Trimetazidine dihydrochlotide | 1 g |
| Lactose | 1500 g |
| Starch | 500 g |
| 10% starch paste | 200 g |
| Starch powder | 20 g |
| Magnesium stearate | 15 g |

Method of Preparation:

Filtrating Levocamitine and trimetaxidine dihydrochloride with 80# mesh screen, mixing it with starch and lactose till in uniform, adding the 10% starch paste, then forming grains with 14# mesh screen, drying at 70□ to 80□, then forming granules with 12# mesh screen, adding starch powder and magnesium stearate, mixing all the ingredients into uniform, and finally forming troche.

| | |
|---|---|
| 1:0.009 | 1000 g:9 g |

Example (22)

Troche of Composition of Levocarnitine and Trimetazidine Dihydrochloride

Formulation (for 1000 Tablets):

| | |
|---|---|
| Levocarnitine | 1000 g |
| Trimetazidine dihydrochlotide | 9 g |
| Lactose | 1500 g |
| Starch | 500 g |
| 10% starch paste | 200 g |
| Starch powder | 20 g |
| Magnesium stearate | 15 g |

Method of Preparation:

Filtrating Levocamitine and trimetaxidine dihydrochloride with 80# mesh screen, mixing it with starch and lactose till in uniform, adding the 10% starch paste, then forming grains with 14# mesh screen, drying at 70□ to 80□, then forming granules with 12# mesh screen, adding starch powder and magnesium stearate, mixing all the ingredients into uniform, and finally forming troche.

| | |
|---|---|
| 1:0.007 | 1000 g:7 g |

Example (23)

Troche of Composition of Levocarnitine and Trimetazidine Dihydrochloride

Formulation (for 1000 Tablets):

| | |
|---|---|
| Levocarnitine | 1000 g |
| Trimetazidine dihydrochlotide | 7 g |
| Lactose | 1500 g |
| Starch | 500 g |
| 10% starch paste | 200 g |
| Starch powder | 20 g |
| Magnesium stearate | 15 g |

Method of Preparation:

Filtrating Levocamitine and trimetaxidine dihydrochloride with 80# mesh screen, mixing it with starch and lactose till in uniform, adding the 10% starch paste, then forming grains with 14# mesh screen, drying at 70□ to 80□, then forming granules with 12# mesh screen, adding starch powder and magnesium stearate, mixing all the ingredients into uniform, and finally forming troche.

| | |
|---|---|
| 1:0.005 | 1000 g:5 g |

Example (24)

Troche Compound of Levocamitine and Trimetazidine Dihydrochloride

Formulation (for 1000 Tablets):

| | |
|---|---|
| Levocarnitine | 1000 g |
| Trimetazidine dihydrochlotide | 5 g |
| Lactose | 1500 g |
| Starch | 500 g |
| 10% starch paste | 200 g |
| Starch powder | 20 g |
| Magnesium stearate | 15 g |

Process of Preparation:

Filtrating Levocamitine and trimetaxidine dihydrochloride with 80# mesh screen, mixing it with starch and lactose till in uniform, adding the 10% starch paste, then forming grains with 14# mesh screen, drying at 70□ to 80□, then forming granules with 12# mesh screen, adding starch powder and magnesium stearate, mixing all the ingredients into uniform, and finally forming troche.

| | |
|---|---|
| 1:0.1 | 1000 g:100 g |

Example (25)

Sustained Release Tablets of Composition of Levocarnitine and Trimetaxidine Dihydrochloride Formulation (for 1000 Tablets):

| | |
|---|---|
| Levocarnitine | 1000 g |
| Trimetazidine dihydrochloride | 100 g |
| Citric acid | 10 g |
| HPMC(K4M) | 160 g |
| Lactose | 180 g |
| Magnesium stearate | 2 mg |

Method of Preparation

Mixing the Levocarnitine, trimetazidine dihydrochloride, lactose and HPMC (K4M) into uniform, dissolving citric acid in ethanol as wetting agent, granulation, drying, and granulation again, adding magnesium stearate and mixing the ingredients well into uniform, and finally forming tablets.

| | |
|---|---|
| 1:0.05 | 1000 g:50 g |

Example (26)

Capsule of Composition of Levocarnitine and Trimetazidine Hydrochloride

Formulation:

| | |
|---|---|
| Levocarnitine | 2000 g |
| trimetazidine | 100 g |
| glutin | 100 g |
| glycerin | 55~66 g |
| Water | 1200 g |
| cod liver oil or refined edible vegetable oil | some |

Method of Preparation

Dissolving Levocarnitine, trimetazidine in cod liver oil or refined edible vegetable oil, and adjusting concentration of each capsule that the quantity of vitamin and Levocarnitine to 90%-120% of the standard quantity, the quantity of vitamin D should be more than 85%, take them as the pharmaceutical solution. Heating glycerin and water to 70° C.~80° C., adding glutin, stirring to dissolving, keeping the temperature for 1-2 hours, removing the floating bubble, filtering, adding into drip pilling machine to drip. Use liquid paraffin as the cooling solution, collecting the cold condensed pills, wiping off the cooling solution with gauze, stay in blowing cold wind at room temperature for 4 hours, baking in oven at 25~35° C. for 4 hours, then washing twice with petroleum ether (3~5 min every time), removing the liquid paraffin around the pills, washing the pills with 95% ethanol once, at last baking at 30~35° C. for about 2 hours, screening, quality testing and packaging.

| | |
|---|---|
| 1:0.02 | 1000 g:20 g |

Example (27)

Suppository of Composition of Levocamitine and Trimetazidine Hydrochloride

Formulation (for 2000 Suppositories):

| | |
|---|---|
| Levocarnitine | 1000 g |
| Trimetazidine dihydrochloride | 20 g |
| Ethyiparaben | 0.5 g |
| 50% alcohol | 100 ml |
| Polysorbate-80 | 100 ml |
| Glycerin-glutin | add up to 3000 g |

Method of Preparation:

Boiling and dissolving Levocamitine, trimetazidine hydrochloride in ethanol, adding ethyiparaben and stirring, further adding some glycerin and stirring to dissolve, slowly pour the mixture in to Glycerin-glutin base, keep the temperature until use. Adding polysorbate-80 and stirring until uniformed, slowly stirring when pouring into the warm base made, well mixing and keeping the temperature at 55° C., casting pouring and cooling until finish.

| | |
|---|---|
| 1:0.1 | 1000 g:100 g |

Example (28)

Suppository of Composition of Levocamitine and Trimetazidine Dihydrochloride

Formulation (for 2000 Suppositories):

| | |
|---|---|
| Levocarnitine | 1000 g |
| Trimetazidine dihydrochloride | 100 g |
| Ethyiparaben | 0.5 g |
| 50% alcohol | 100 ml |
| Polysorbate-80 | 100 ml |
| Glycerin-glutin | add up to 3000 g |

Method of Preparation:

Boiling and dissolving Levocarnitine, trimetazidine hydrochloride in ethanol, adding ethyiparaben and keep stirring, further adding some glycerin and stirring to dissolve, slowly pour the mixture in to Glycerin-glutin base, keep the temperature warm until use. Adding polysorbate-80 and stirring until uniformed, slowly stirring when pouring into the warm base made, well mixing and keeping the temperature at 55° C., casting pouring and cooling until finish.

| | |
|---|---|
| 1:0.2 | 1000 g:200 g |

Example (29)

Suppository of Composition of Levocarnitine and Trimetazidine Dihydrochloride Formulation (for 2000 Suppositories):

| | |
|---|---|
| Levocarnitine | 1000 g |
| Trimetazidine dihydrochloride | 200 g |
| Ethyiparaben | 0.5 g |
| 50% alcohol | 100 ml |
| Polysorbate-80 | 100 ml |
| Glycerin-glutin | add up to 3000 g |

Method of Preparation:

Boiling and dissolving Levocarnitine, trimetazidine hydrochloride in ethanol, adding ethyiparaben and keep stirring, further adding some glycerin and stirring to dissolve, slowly pour the mixture in to Glycerin-glutin base, keep the temperature warm until use. Adding polysorbate-80 and stirring until uniformed, slowly stirring when pouring into the warm base made, well mixing and keeping the temperature at 55° C., casting pouring and cooling until finish

| | |
|---|---|
| 1:0.4 | 1000 g:400 g |

Example (30)

Suppository of Composition of Levocarnitine and Trimetazidine Dihydrochloride Formulation (for 2000 Suppositories):

| | |
|---|---|
| Levocarnitine | 1000 g |
| Trimetazidine dihydrochloride | 400 g |
| Ethyiparaben | 0.5 g |
| 50% alcohol | 100 ml |
| Polysorbate-80 | 100 ml |
| Glycerin-glutin | add up to 3000 g |

Method of Preparation:

Boiling and dissolving Levocarnitine, trimetazidine hydrochloride in ethanol, adding ethyiparaben and keep stirring, further adding some glycerin and stirring to dissolve, slowly pour the mixture in to Glycerin-glutin base, keep the temperature warm until use. Adding polysorbate-80 and stirring until uniformed, slowly stirring when pouring into the warm base made, well mixing and kept the temperature at 55° C., casting pouring and cooling until finish.

Example 4

The Composition Packaging of Levocarnitine Pharmaceutical Preparation and Trimetazidine Hydrochloride Pharmaceutical Preparation Preparing or purchasing of pharmaceutical preparations of Levocarnitine and trimetazidine hydrochloride respectively, this has shown in table 5.

TABLE 5

Different specifications of pharmaceutical preparations of Levocarnitine and trimetazidine hydrochloride

| Levocarnitine preparation | trimetazidine hydrochloride preparation |
|---|---|
| Injection 0.5 g | trimetazidine dihydrochloride tablet 2 mg |
| Injection 1 g | trimetazidine dihydrochloride tablet 3 mg; |
| Injection 2 g | trimetazidine dihydrochloride coated Tablets 20 mg |
| Oral tablet 0.25 g | trimetazidine hydrochloride Sustained-release Tablets 35 mg |
| Oral tablet 0.333 g | trimetazidine hydrochloride injection 2 ml: 4 mg |
| Oral tablet 0.5 g | |
| Oral tablet 1 g | |
| Oral Liquid 2.5 ml: 0.25 g | |
| Oral Liquid 5 ml: 0.5 g | |
| Oral Liquid 10 ml: 1 g | |
| Oral Liquid 50 ml: 5 g | |
| Oral Liquid 100 ml: 10 g | |
| Oral Liquid 500 ml: 50 g | |

Combining any preparation of Levocarnitine such as 0.5 g of injection form, together with five kinds of preparations of trimetazidine hydrochloride, total will be 65 kinds of composition packaging. The packing experiment here only followed ratio at 1:1. In reality, the amount of preparations in the each composition packaging can be varied based on the needs of clinic.

We claim:

1. A pharmaceutical composition, comprising a) levocarnitine or its derivatives, and b) trimetazidine or its pharmaceutical acceptable salts; wherein the dosage of a) and b) of the composition is effective in treating myocardial ischemia and reducing the area of myocardial infarction, and wherein the weight ratio of a) and b) is 1:0.000016-1:0.4.

2. The pharmaceutical composition of claim 1, wherein the Levocarnitine or its derivatives is selected from the group consisting of Levocarnitine, propionyl Levocarnitine, acetyl Levocarnitine and their pharmaceutical acceptable salts.

3. The pharmaceutical composition of claim 1, wherein pharmaceutical acceptable salts of the trimetazidine and Levocarnitine or its derivatives include hydrochloride salt, hydrobromide, iodate, sulfate, nitrate, phosphate, acetate, maleate, fumarate salt, citrate, oxalate, succinate, tartrate, malate, mandelate, trifluoromethyl acetate, pantothenate, methanesulfonate, or toluenesulfanate.

4. The pharmaceutical composition of claim 1, wherein the pharmaceutical acceptable salts are salts of acids capable of forming a salt with the trimetazidine or forming a salt with levocarnitine or its derivatives.

5. The pharmaceutical composition of claim 3, wherein the acids selected from the group consisting of hydrochloride acid, hydrobromide acid, hydriodic acid, sulphuric acid, nitric acid, phosphoric acid, acetic acid, maleic acid, maleic acid, maleic acid, oxalic acid, oxalic acid, tartaric acid, malic acid, mandelic acid, trifluoroacetic acid, pantothenic acid, methane sulfonic acid, and para-toluenesulfonic acid.

6. The pharmaceutical composition of claim 1, wherein the pharmaceutical composition contains Levocarnitine and hydrochloride salt of trimetazidine in a weight ratio of about 1:0.005.

7. The pharmaceutical composition of claim 1, further comprising one or more pharmaceutical acceptable carriers for a pharmaceutical preparation, the pharmaceutical preparation selected from oral administration, injected administration or local administration.

8. The pharmaceutical composition of claim 7, wherein the pharmaceutical preparation is an oral administration form selected from a tablet, sustained-release tablet, granule, solid or soft capsule, syrup, solution, emulsion; an injection administration form selected from an aseptic solution or aseptic oil in water micro-emulsion or aseptic powder; or a local administration form selected from patches, suppositories, cream, ointment, gelatin, solution or suspension.

9. The pharmaceutical composition of claim 1, which is effective for treating myocardial ischemia, heart pump failure, cardiogenic shock, chronic myocardial infarction, angina, acute coronary syndrome, acute/chronic heart failure, and myocardial metabolic disorder which caused by myocardial ischemia.

10. The pharmaceutical composition of claim 1, which is effective for reducing area of myocardial infarction.

11. A method for treating myocardial ischemia, the method comprising:
administering successively or simultaneously to a patient a composition comprising trimetazidine or its pharmaceutical acceptable salts and a composition comprising Levocarnitine or its derivatives.

12. A method for treating myocardial ischemia, the method comprising:
administering to a patient the pharmaceutical composition of claim 1.

13. A method for treating myocardial ischemia, the method comprising:
administering to a patient the pharmaceutical composition of claim 2.

14. A method for treating myocardial ischemia, the method comprising:
administering to a patient the pharmaceutical composition of claim 3.

15. A method for treating myocardial ischemia, the method comprising:
administering to a patient the pharmaceutical composition of claim 6.

16. A method for treating myocardial ischemia, the method comprising:
administering to a patient the pharmaceutical composition of claim 7.

17. A method of using a pharmaceutical composition in the manufacture of a medicament, the pharmaceutical composition comprising levocarnitine or its derivatives thereof and trimetazidine or its pharmaceutical acceptable salts, the method comprising
providing the pharmaceutical composition, and
making a medicament comprising the pharmaceutical composition,
wherein the medicament provides a dose of adults per day (a) from 10 mg to 600 mg/kg weight of Levocarnitine or its derivatives, and (b) from 0.01 mg to 3 mg/kg body weight of trimetazidine or its pharmaceutical acceptable salt, the Levocarnitine or its derivative and trimetazidine or its pharmaceutically acceptable salt having a weight ratio from about 1:0.000016 to about 1:0.3.

18. A method of using a pharmaceutical composition in the manufacture of a medicament, the pharmaceutical composition comprising levocarnitine or its derivatives thereof and trimetazidine or its pharmaceutical acceptable salts, the method comprising
providing the pharmaceutical composition, and
making a medicament comprising the pharmaceutical composition,
wherein the medicament provides a dose of adults per day (a) from 1000 mg to 30000 mg Levocarnitine or its derivatives, and (b) from 1 mg to 60 mg trimetazidine or its pharmaceutical acceptable slat, the Levocarnitine or its derivative and trimetazidine or its pharmaceutically acceptable salt having a weight ratio from about 1:0.000016 to about 1:0.3.

19. A method of using a pharmaceutical composition in the manufacture of a medicament, the pharmaceutical composition comprising levocarnitine or its derivatives thereof and trimetazidine or its pharmaceutical acceptable salts, the method comprising
providing the pharmaceutical composition, and
making a medicament comprising the pharmaceutical composition,
wherein the medicament provides a dose of adults per day (a) from 10 mg to 600 mg/kg weight of Levocarnitine or its derivatives, and (b) from 0.01 mg to 3 mg/kg weight of trimetazidine and its pharmaceutically acceptable salt, the Levocarnitine or its derivative and trimetazidine or its pharmaceutically acceptable salt having a weight ratio of about 1:0.005.

20. A method of using a pharmaceutical composition in the manufacture of a medicament, the pharmaceutical composition comprising levocarnitine or its derivatives thereof and trimetazidine or its pharmaceutical acceptable salts, the method comprising
providing the pharmaceutical composition, and
making a medicament comprising the pharmaceutical composition,
wherein the medicament provides a dose of adults per day (a) from 1000 mg to 30000 mg Levocarnitine or its derivatives, and (b) from 1 mg to about 60 mg trimetazidine and its pharmaceutically acceptable salt, the Levocarnitine or its derivative and trimetazidine or its pharmaceutically acceptable salt having a weight ratio of about 1:0.005.

* * * * *